US011344509B2

(12) United States Patent
Behnam

(10) Patent No.: US 11,344,509 B2
(45) Date of Patent: *May 31, 2022

(54) SOLUBILIZATE WITH CURCUMIN AND BOSWELLIA AND XANTHOHUMOL

(71) Applicant: Aquanova AG, Darmstadt (DE)

(72) Inventor: Dariush Behnam, Rossdorf (DE)

(73) Assignee: Aquanova AG, Darmstadt (DE)

( * ) Notice: Subject to any disclaimer, the term of this patent is extended or adjusted under 35 U.S.C. 154(b) by 52 days.

This patent is subject to a terminal disclaimer.

(21) Appl. No.: 16/629,077

(22) PCT Filed: Jul. 11, 2018

(86) PCT No.: PCT/EP2018/068729
§ 371 (c)(1),
(2) Date: Jan. 7, 2020

(87) PCT Pub. No.: WO2019/011954
PCT Pub. Date: Jan. 17, 2019

(65) Prior Publication Data
US 2020/0222346 A1 Jul. 16, 2020

(30) Foreign Application Priority Data

| Jul. 11, 2017 | (DE) | 10 2017 115 496.5 |
| Jul. 11, 2017 | (WO) | PCT/EP2017/067381 |
| Jul. 11, 2017 | (WO) | PCT/EP2017/067382 |

(51) Int. Cl.
| A61K 31/12 | (2006.01) |
| A61K 9/107 | (2006.01) |
| A61K 9/48 | (2006.01) |
| A61K 31/05 | (2006.01) |
| A61K 31/122 | (2006.01) |
| A61K 31/19 | (2006.01) |
| A61K 38/48 | (2006.01) |
| A61K 47/26 | (2006.01) |

(52) U.S. Cl.
CPC ............ *A61K 31/12* (2013.01); *A61K 9/1075* (2013.01); *A61K 9/48* (2013.01); *A61K 31/05* (2013.01); *A61K 31/122* (2013.01); *A61K 31/19* (2013.01); *A61K 38/4886* (2013.01); *A61K 47/26* (2013.01)

(58) Field of Classification Search
CPC ........ A61K 31/12; A61K 31/19; A61K 31/05; A61K 31/122
See application file for complete search history.

(56) References Cited

U.S. PATENT DOCUMENTS

| 5,629,351 A | 5/1997 | Taneja et al. |
| 5,972,382 A | 10/1999 | Majeed et al. |
| 11,197,834 B2 * | 12/2021 | Behnam .................. A61P 3/06 |
| 2008/0220102 A1 | 9/2008 | Behnam |
| 2009/0087419 A1 | 4/2009 | Sakai et al. |
| 2009/0208472 A1 | 8/2009 | Sakai et al. |
| 2010/0029757 A1 | 2/2010 | Hellerbrand |
| 2011/0086017 A1 | 4/2011 | Kravets et al. |
| 2011/0129546 A1 | 6/2011 | Mill |
| 2011/0293678 A1 | 12/2011 | Behnam |
| 2015/0342881 A1 | 12/2015 | Behnam |
| 2016/0008298 A1 | 1/2016 | Stevens |
| 2016/0022569 A1 | 1/2016 | Tonge et al. |
| 2016/0074316 A1 | 3/2016 | Caetano et al. |
| 2016/0081975 A1 | 3/2016 | Bromley |
| 2017/0042835 A1 | 2/2017 | Singh |
| 2019/0314326 A1 | 10/2019 | Garti et al. |
| 2020/0129452 A1 | 4/2020 | Behnam |
| 2020/0222346 A1 | 7/2020 | Behnam |

FOREIGN PATENT DOCUMENTS

| DE | 102006024911 A1 | 11/2007 |
| DE | 102006062264 A1 | 6/2008 |
| DE | 202012012130 U1 | 3/2014 |
| EP | 0755940 A1 | 1/1997 |
| EP | 1431385 A1 | 6/2004 |
| EP | 2018869 A1 | 1/2009 |
| JP | H07165588 A | 6/1995 |
| JP | H11500725 A | 1/1999 |
| JP | 2011524884 A | 9/2011 |
| JP | 2016505579 A | 2/2016 |
| RU | 2530056 C2 | 10/2014 |
| WO | 03092664 A1 | 11/2003 |
| WO | 2005092352 A1 | 10/2005 |

(Continued)

OTHER PUBLICATIONS

Benham, Copending U.S. Appl. No. 17/258,363, filed Jan. 6, 2021.
Benham, Copending U.S. Appl. No. 17/258,397, filed Jan. 6, 2021.
Benham, Copending U.S. Appl. No. 17/258,409, filed Jan. 6, 2021.
Alexa Kocher et al, "The oral bioavailability of curcuminoids in healthy humans is markedly enhanced by micellar solubilisation but not further improved by simultaneous ingestion of sesamin, ferulic acid, naringenin and xanthohumol", Journal of Functional Foods, vol. 14, Apr. 1, 2015 (Apr. 1, 2015), p. 183-191.
Bhagat Shivani, Agarwal Monika, Roy Vandana, "Serratiopeptidase: A systematic review of the existing evidence", International Journal Of Surgery, Feb. 1, 2013, Surgical Associates, London, GB, Source info: vol. 11, Nr: 3, pp. 209-217.

(Continued)

*Primary Examiner* — Kevin E Weddington
(74) *Attorney, Agent, or Firm* — Smartpat PLC

(57) ABSTRACT

A solubilizate comprises curcumin in a content of less than or equal to 10 wt %, preferably less than or equal to 8 wt %, most preferably 3 wt % to 7 wt %, one or more *Boswellia* acids and/or one or more *Boswellia* acid derivatives in a total content of less than or equal to 10 wt %, preferably less than or equal to 8 wt %, most preferably 4.7 wt % to 6.6 wt %, xanthohumol in a content of less than or equal to 10 wt %, preferably less than or equal to 5 wt %, most preferably 1 wt % to 3 wt %, and at least one emulsifier with an HLB value in a range of less than 18, preferably between 13 and 18, in particular polysorbate 80 or polysorbate 20 or a mixture of polysorbate 20 and polysorbate 80.

21 Claims, No Drawings

(56) References Cited

FOREIGN PATENT DOCUMENTS

| WO | 2007006497 A2 | 1/2007 |
| WO | 2007058480 A1 | 5/2007 |
| WO | 2008065451 A2 | 6/2008 |
| WO | 2014094921 A1 | 6/2014 |
| WO | 2015171445 A1 | 11/2015 |
| WO | 2016022936 A1 | 2/2016 |
| WO | 2018061007 A1 | 4/2018 |

OTHER PUBLICATIONS

Ch. Schiborr et al., "The oral bioavailability of curcumin from micronized powder and liquid micelles is significantly increased in healthy humans and differs between sexes", Molecular Nutrition & Food Research, (20140000), vol. 0, pp. 1-12.

Dorn et al., "Increased expression of c-Jun in nonalcoholic fatty liver disease", Lab Invest., (20140000), vol. 94, pp. 394-408.

F. Capasso et al., "Glycyrrhetinic acid, leucocytes and prostaglandins", J. Pharm. Pharmacol. 1983, 35: 332-335.

Hellebrand et al., "Promoterhypermethylation is causing functional relevant downregulation of methylthioadenosine phosphorylase (MTAP) expression in hepatocellular carcinoma", Carcinogenesis, (20060000), vol. 27, pp. 64-72.

K. Gerbeth et al., "Determination of major boswelic acids in plasma by high-pressure liquid chromatography/mass spektrometry", Journal of Pharmaceutical and Biomedical Analysis, vol. 56, No. 5, pp. 998-1005.

Kerstin Gross-Steinmeyer, Patricia L Stapleton, Julia H Tracy, Theo K Bammler, Stephen C Strom, Donald R Buhler, David L Eaton, "Modulation of Aflatoxin B1-Mediated Genotoxicity in Primary Cultures of Human Hepatocytes by Diindolylmethane, Curcumin, and Xanthohumols", Toxicological Sciences,,Dec. 1, 2009,Academic Press, vol. 112, Nr: 2, pp. 303-310.

Khayyal M T, "Novel formulations of Curcumin, Boswellia and Xanthohumol extracts markedly enhance their individual and combined anti-inflammatory activity", EMBASE01 Sep. 2017 (Sep. 1, 2017), Database accession No. EMB-621379886, Retrieved from the Internet: URL:Elsevier Science Publishers, Amsterdam, NL, XP002783955, 1-20 the whole document & Zeitschrift Fur Phytotherapie Sep. 1, 2017 Hippokrates Verlag GMBH NLD,vol. 38, No. Supplement 1, Sep. 1, 2017 (Sep. 1, 2017).

Lini Alappat, Atif B Awad, "Curcumin and obesity: evidence and mechanisms", Nutrition Reviews,,Dec. 1, 2010, International Life Sciences Institute, vol. 68, Nr: 12, pp. 729-738.

Liu, Chen et al., "Enhanced skin permeation of glabridin using eutectic mixture-based nanoemulsion", Drug Deliv. Transl. Res., 2017, vol. 7, pp. 325-332.

Manju Rawat Singh, Singh Deependra, Swarnlata Saraf, "Development and in vitro evaluation of polar lipid based lipospheres for oral delivery of peptide drugs", International Journal of Drug Delivery,,Jul. 31, 2009, vol. 1, Nr: 1, pp. 15-26.

Manju Rawat, Swarnlata Saraf, "Formulation optimization of double emulsification method for preparation of enzyme-loaded Eudragit S100 microspheres", Journal Of Microencapsulation, Jun. 1, 2009,Taylor And Francis, Basingstoke, GB, vol. 26, Nr: 4, pp. 306-314.

Pearson, "Development of Arthritis, Periarthritis and Periostitis in Rats Given Adjuvants". Proceedings of the Society tor Experimental Biology and Medicine, vol. 91 issue: 1, pp. 95-101Issue published: Jan. 1, 1956.

Raju Gautam, Sanjay M Jachak, "Recent developments in antiinflammatory natural products", Publication data: Medicinal Research Reviews, Sep. 1, 2009, New York, NY, US, Source info: vol. 29, Nr: 5, pp. 767-820.

Reji Kizhakkedath, "Clinical evaluation of a formulation containing Curcuma longa and Boswellia serrata extracts in the management of knee osteoarthritis", Molecular Medicine Reports,vol. 8, No. 5, Nov. 1, 2013 (Nov. 1, 2013), pp. 1542-1548.

U. Siemoneit et al., "Inhibition of microsomal prostaglandin E-synthase-1 as a molecular basis for the antiinflammatory actions of boswellic acids from frankincense", British Journal of Pharmacology, vol. 162, No. 1, pp. 147-162.

Wobser et al., "Lipid accumulation in hepatocytes induces fibrogenic activation of hepatic stellate cells", Cell Res, (20090000), vol. 19, pp. 996-1005.

Y. Tominaga et al.: "Licorice flavonoid oil effects body weight loss by reduction of body fat mass in overweight subjects", Journal of Health Science 52(6), 2006, pp. 672-683.

Y. Tominaga et al.: "Licorice flavonoid oil reduced total body fat and visceral fat in overweight subjects: A randomized, double-blind, placebo-controlled study", Obesity Research & Clinical Practice (3), 2009, pp. 169-178.

Zamzow Daniel R et al, "Xanthohumol improved cognitive flexibility in young mice", Behavioural Brain Research,vol. 275, Sep. 1, 2014 (Sep. 1, 2014), p. 1-10.

Zeitschrift Fur Phytotherapie Sep. 1, 2017 Hippokrates Verlag GMBH NLD, Sep. 1, 2017, vol. 38, Supplement 1, ISSN 1438-9584, Abstract.

\* cited by examiner

SOLUBILIZATE WITH CURCUMIN AND BOSWELLIA AND XANTHOHUMOL

TECHNICAL FIELD

The disclosure relates to a solubilizate comprising curcumin and *Boswellia* and xanthohumol. Furthermore, the disclosure relates to a fluid containing such a solubilizate, to a capsule filled with such a solubilizate or fluid, and to a dietary supplement and/or pharmaceutical drug containing such a solubilizate.

BACKGROUND

Curcumin is discussed as an active substance based on various potential pharmacological properties. For example, there are indications for the antioxidant and also for the anti-inflammatory effect of curcumin as well as for the effectiveness against viruses and bacteria as well as against cancer. Indications could therefore be, for example, Parkinson's, Alzheimer's, diabetes, colorectal tumors, pancreatic cancer, and liver dysfunction.

In order to be able to enter the bloodstream after oral intake, the active substance must pass through the small intestinal blood barrier, is then metabolized in the liver and enters the hepatic vein as a bioavailable fraction. The rest of the total active substance ingested and released in the body is either degraded microbially in the intestine or eliminated with the faeces or bile.

A toxicity due to the micellization of the active substance according to the disclosure in comparison to the native form could be ruled out on the basis of studies with MTT assays for cell viability. The verification of cell vitality by MTT assay is based on the reduction of the yellow water-soluble dye 3-(4,5-dimethylthiazol-2-yl)-2,5-diphenyltetrazolium bromide (MTT) into a blue-violet water-insoluble formazan.

The extract from the resin of the frankincense tree, *Boswellia serrata* extract, contains several pentacyclic triterpenes which together are often referred to as total boswellic acids ("total BAs"). The term "boswellic acids" refers to a group of chemical compounds naturally occurring in the resin of the frankincense trees mentioned above. The two basic structures are $\alpha$-boswellic acid and $\beta$-boswellic acid. Also, some derivatives of the boswellic acids are known, in particular compounds which carry a keto group at position 11 and/or which are acetylated at position 3. Boswellic acids that are currently considered to be significant in terms of pharmacological effects in particular include $\alpha$-boswellic acid ($\alpha$BA) and $\beta$-boswellic acid ($\beta$BA) and their derivatives 11-keto-$\beta$-boswellic acid (KBA); CAS 17019-92-0) and 3-O-acetyl-11-keto-$\beta$-boswellic acid (AKBA); CAS 67416-16-9), and 3-O-acetyl-$\alpha$-boswellic acid (A$\alpha$BA), and 3-O-acetyl-$\beta$-boswellic acid (A$\beta$BA). In particular the derivative AKBA is considered to have an anti-inflammatory effect.

In the context of the present application, the term "*Boswellia*", in particular in the term "*Boswellia* solubilizate" is used in the sense that the term "*Boswellia*" refers to the active substances from the resin of the frankincense tree, i.e. to at least one boswellic acid and/or at least one derivative of a boswellic acid. The term "boswellic acid solubilizate" refers to a micellar formulation of at least one boswellic acid which may also contain at least one boswellic acid derivative.

Xanthohumol is a flavonoid naturally occurring in hops. It is a prenylated plant polyphenol which is assigned to the chalcones and has only been identified in hops so far. The bitter hop varieties have a significantly higher content of xanthohumol than aroma varieties. In tests, xanthohumol was found to be effective against the emergence and development of cancer cells. In laboratory experiments, it was moreover found that xanthohumol is capable of protecting the nerve cells of the brain and thus could possibly help to slow down the course of diseases like Alzheimer's or Parkinson's.

For example, http://www.besserlaengerleben.at/gesund-und-fit/hopfen-hilft-gegen-cholesterin-und-blutzucker.html reports about studies according to which xanthohumol seems to lower plasma levels of PCSK9, a protein that plays an important role in cholesterol levels. A reduction in PCSK9 levels could improve the decomposition of LDL cholesterol from the blood. Scientists at Oregon State University have shown in laboratory animals that the intake of large amounts of xanthohumol can lead to improvements in metabolic syndrome and reduced weight gain. These research results could lead to new approaches in treating obesity, high cholesterol and high blood sugar. The combination of these health problems, known as the metabolic syndrome, is nowadays one of the leading causes of death in industrialized countries, besides cardiovascular diseases and type 2 diabetes.

Xanthohumol occurs naturally in hops and therefore in beer. The highest levels used in the study would be equivalent to a human dose of 350 milligrams per day for one person. However, this value clearly exceeds what can be achieved by normal intake of food. However, intake through a dietary supplement would theoretically be possible without problems.

Hop extracts are currently commercially available as dietary supplements. However, it has been found that the bioavailability of xanthohumol is low when the hops extracts are taken orally.

For the purposes of the present application, the term "active substance" refers to a substance that is provided in a pharmaceutically effective concentration and is preferably added for the purpose of having a pharmaceutical effect. Here, the name of the respective active substance is understood to encompass also substances that are converted in the body into the active substance and/or into its biologically active form.

SUMMARY

The inventor has therefore set itself the task of providing a formulation which makes the health-promoting or curative properties of curcumin and *Boswellia* and xanthohumol available for the human or animal organism. In particular, it is an object of the disclosure to provide for a highest possible bioavailability of curcumin and *Boswellia* and xanthohumol.

These objects are achieved in a surprisingly simple way with a solubilizate as claimed. This solubilizate contains curcumin in a content of less than or equal to 10 wt %, preferably less than or equal to 8 wt %, most preferably 3 wt % to 7 wt %; one or more *Boswellia* acids and/or one or more *Boswellia* acid derivatives in a total content of less than or equal to 10 wt %, preferably less than or equal to 8 wt %, most preferably 4.7 wt % to 6.6 wt %; xanthohumol in a content of less than or equal to 10 wt %, preferably less than or equal to 5 wt %, most preferably 1 wt % to 3 wt %; and at least one emulsifier with an HLB value in a range of less than 18, preferably between 13 and 18, in particular polysorbate 80 or polysorbate 20 or a mixture of polysorbate 20 and polysorbate 80.

In a preferred embodiment, the solubilizate consists of curcumin in a content of less than or equal to 10 wt %, preferably less than or equal to 8 wt %, most preferably 3 wt % to 7 wt %; one or more *Boswellia* acids and/or one or more *Boswellia* acid derivatives in a total content of less than or equal to 10 wt %, preferably less than or equal to 8 wt %, most preferably 4.7 wt % to 6.6 wt %; xanthohumol in a content of less than or equal to 10 wt %, preferably less than or equal to 5 wt %, most preferably 1 wt % to 3 wt %; and at least one emulsifier with an HLB value in a range of less than 18, preferably between 13 and 18, in particular polysorbate 80 or polysorbate 20 or a mixture of polysorbate 20 and polysorbate 80.

Due to the high proportion of *Boswellia*, the disclosure contemplates, in an advantageous embodiment thereof, that the solubilizate contains an extract obtained from the resin of the plant *Boswellia serrata* by extraction using ethyl acetate as a source of the one or more boswellic acids and/or one or more boswellic acid derivatives, wherein boswellic acids are contained in a concentration of at least 85 wt % in this extract.

It has been found that, depending on how much *Boswellia* is to be solubilized and in particular also depending on the question of whether further active substances are to be micellated in addition to *Boswellia*, the mass ratio of emulsifier to boswellic acids and/or to boswellic acids and at least one of their derivatives is in a range between 20:1 and 3:1, preferably in a range between 16:1 and 4:1, preferably in a range between 14:1 and 5:1.

Due to the high proportion of xanthohumol, an advantageous embodiment of the solubilizate contains an ethanolic extract of hard resins from hops as a source of xanthohumol, with a xanthohumol concentration in this extract in a range between 65 wt % and 95 wt %, preferably in a concentration in a range from 80% to 92 wt %. In particular the product "Xantho-Flav Pure" that will be discussed in more detail below can be used as a xanthohumol source in the context of the disclosure.

It has been found that, depending on how much xanthohumol is to be solubilized and in particular also depending on the question of whether further active substances are to be micellated in addition to xanthohumol, the mass ratio of emulsifier, in particular polysorbate 80, to xanthohumol is in a range between 30:1 and 3:1, preferably in a range between 25:1 and 5:1, preferably in a range between 9.8:1 and 6.6:1.

Depending on how much curcumin is to be provided in micellated form in addition to *Boswellia* and xanthohumol in the solubilizate comprising curcumin and *Boswellia* and xanthohumol, the ratio of emulsifier to curcumin may be chosen in a range between 30:1 and 3:1, preferably in a range between 25:1 and 9:1, preferably in a range between 23:1 and 12:1. Accordingly, the ratio of emulsifier to boswellic acids and/or to boswellic acids and at least one of their derivatives may be in the range between 20:1 and 3:1, preferably in the range between 16:1 and 4:1, preferably in the range between 14:1 to 5:1, and the ratio of emulsifier, in particular of polysorbate 80, to xanthohumol may be in the range between 30:1 and 3:1, preferably in the range between 25:1 and 5:1, preferably in the range between 9.8:1 and 6.6:1

For a stable micellization of curcumin and *Boswellia* in the solubilizate, it has proven to be advantageous if the ratio of emulsifier to the total mass of curcumin and boswellic acids and/or of curcumin and boswellic acids and at least one of their derivatives is in the range between 15:1 and 3:1, preferably in the range between 10:1 and 4:1, preferably in the range between 8.8:1 and 5.7:1.

To this end, the emulsifier content, in particular the polysorbate content, is at least 70 wt %, preferably in the range between 75 wt % and 95 wt %, most preferably in the range between 79 wt % and 88 wt %.

Depending on how much emulsifier can be used for a specific application purpose of the solubilizate, the disclosure offers the possibility for the solubilizate to contain up to 20 wt %, preferably up to 15 wt % of ethanol. The addition of ethanol allows to reduce the content of polysorbate, which is an advantage with regard to the ADI value for polysorbate.

Depending on which active substances are to be solubilized and in what quantity, it may be helpful for the formation of stable micelles if the solubilizate contains up to 25 wt %, preferably up to 10 wt % of glycerol. The addition of glycerol also allows to reduce the content of polysorbate.

The solubilizates exhibit a narrow particle size distribution with small mean particle size, even under the physiological conditions of a gastric passage; the distribution of the diameter of the micelles in a dilution of the solubilizate with distilled water in a ratio of 1:500 under physiological conditions (pH 1.1 and 37° C.) ranges from about $d_{10}$=6 nm to about $d_{90}$=16 nm. These values were determined from a volume distribution. Details regarding the particle size analysis of the micelles of the solubilizates will be explained below.

The disclosure advantageously provides solubilizates having very good anti-inflammatory properties. The anti-inflammatory activity, measured as a concentration of C-reactive protein (CRP) in the blood serum of arthritic rats after a single administration of the solubilizate in a dose of 5 mg/kg body weight of curcumin and 10 mg/kg body weight of boswellic acids is in a range from about 1200 pg/mL to about 1500 pg/mL, compared to between about 3200 pg/mL and about 3500 pg/mL after administration of the same dose of native curcumin and *Boswellia*, respectively.

The anti-inflammatory effect of the disclosure solubilizate comprising curcumin and *Boswellia*, measured as the concentration of myeloperoxidase (MPO) in the blood serum of arthritic rats after a single administration of the solubilizate in a dose of 5 mg/kg body weight of curcumin and 10 mg/kg body weight of boswellic acids is in a range from about 750 mU/mL to about 815 mU/mL and thus is significantly lower than the about 1150 mU/mL to about 1250 mU/mL after administration of the same dose of native curcumin and *Boswellia*, respectively.

The enzyme unit (U) is a unit which has since been replaced by the katal (kat) to indicate enzymatic activity. Since the numerical values change when katal is used, the enzyme unit (U) continues to be used in medicine and clinical chemistry. One enzyme unit U corresponds to one micro-mole substrate conversion per minute.

An indication of the improved bioavailability compared to compositions comprising *Boswellia* and curcumin which have not been micellated is obtained by a measurement of turbidity of the solubilizate, which is much easier accessible to measurement techniques. As a result of the formulation according to the disclosure, the turbidity of the solubilizate is preferably less than 25 FNU, more preferably less than 3 FNU, measured by scattered light measurement using infrared light according to the specifications of the ISO 7027 standard at a dilution of the solubilizate in a ratio of 1:500 in water under physiological conditions (pH 1.1 and 37° C.).

In the context of the disclosure, the solubilizate may contain the xanthohumol in non-solubilized form, in particular in native form. Such a product is obtained when adding a xanthohumol-containing powder, for example a hops extract, into a solubilizate as described above. As a result, the solubilizate contains active substances such as *Boswellia* and curcumin in solubilized form, that is to say in the form of micelles, and additionally xanthohumol in non-solubilized form, that is to say not included in micelles. In this case, xanthohumol as a dispersed phase may be surrounded by an emulsifier envelope, for example in the form of emulsion drops or particles of a suspoemulsion with the other solubilizate as a continuous phase.

In order to facilitate oral application of the solubilizate in a more simple and convenient way for the consumer or patient, the disclosure also provides a capsule filled with a solubilizate as described above or with a corresponding solubilizate comprising curcumin, boswellic acid, and xanthohumol, wherein the capsule is in the form of a soft gelatin capsule or a hard gelatin capsule or a soft gelatin-free capsule or a hard gelatin-free capsule, for example a cellulose capsule.

Moreover, the solubilizate may be incorporated into other fluids, in particular liquids. The active substance-filled small micelles will be retained in this case. Thus, the disclosure also provides a fluid containing the solubilizate as described above, wherein the fluid is selected from the group consisting of foods, beverages, cosmetics, and pharmaceutical products. In the context of the disclosure, the fluid may in particular comprise an aqueous dilution of the solubilizate.

The disclosure thus also allows to use a solubilizate or fluid as described above in a particularly simple way as a dietary supplement and/or as a pharmaceutical drug for treating and/or preventing diseases involving inflammation, cancer, Alzheimer's, Parkinson's, obesity, high cholesterol, high blood sugar, metabolic syndrome and/or autoimmune diseases.

The disclosure furthermore provides a method for treating and/or preventing diseases involving inflammation, cancer, Alzheimer's, Parkinson's, obesity, high cholesterol, elevated blood sugar, metabolic syndrome, and/or autoimmune diseases, which comprises administering to the patient, in particular orally, a solubilizate according to the disclosure, in particular in a capsule or as a fluid. In a preferred embodiment of the method, the solubilizate is administered to the patient in a curcumin dose ranging from 0.5 mg/kg body weight to 1 mg/kg body weight, preferably in a dose of 0.81 mg/kg body weight, and in a *Boswellia* dose ranging from 1 mg/kg body weight to 2 mg/kg body weight, preferably in a dose of 1.62 mg/kg body weight, in particular once daily, and in a xanthohumol dose ranging from 0.5 mg/kg body weight to 1 mg/kg body weight, preferably in a dose of 0.81 mg/kg body weight.

For producing a solubilizate comprising curcumin and *Boswellia* and xanthohumol as the active substances it is possible to either mix together individually prepared solubilizates, or to directly prepare a solubilizate containing curcumin and *Boswellia* and xanthohumol.

The disclosure furthermore provides methods for producing a solubilizate as described above. If co-micellization of *Boswellia* with curcumin and xanthohumol is desired, the disclosure provides the following variant of a preparation method, comprising the steps of (a) providing polysorbate 80 and/or polysorbate 20 and/or a mixture of polysorbate 20 and polysorbate 80;
(b) adding *Boswellia serrata* extract powder and an ethanolic extract of hard resins from hops, in particular Xantho-Flav Pure powder and/or Xantho-Flav powder;
(c) adding curcumin powder;
wherein step (a) comprises heating to a temperature in the range from 40° C. to 62° C., preferably to a temperature in the range from 45° C. to 57° C., most preferably to a temperature in the range from 48° C. to 52° C.; and
wherein step (b) comprises heating to a temperature in the range from 60° C. to 75° C., preferably to a temperature in the range from 61° C. to 70° C., most preferably to a temperature in the range from 63° C. to 67° C.; and
wherein step (c) comprises heating to a temperature in the range from 82° C. to 97° C., preferably to a temperature in the range from 83° C. to 92° C., most preferably to a temperature in the range from 85° C. to 89° C.

This preparation method allows to produce a solubilizate which is able to form micelles loaded with curcumin as well as with boswellic acids and with xanthohumol in an aqueous dilution. For this purpose, it is also possible to mix the two active substances with one another in a preparatory step under appropriately adapted temperature control, and then to add them in combined form, as a mixture.

However, it is also possible within the scope of the disclosure to provide native xanthohumol in a solubilizate comprising curcumin and boswellic acids. For this purpose, the disclosure provides the following variant of a preparation method, comprising the steps of (a) providing polysorbate 80 and/or polysorbate 20 and/or a mixture of polysorbate 20 and polysorbate 80;
(b) adding *Boswellia serrata* extract powder;
(c) adding curcumin powder;
wherein step (a) comprises heating to a temperature in the range from 40° C. to 62° C., preferably to a temperature in the range from 45° C. to 57° C., most preferably to a temperature in the range from 48° C. to 52° C.; and
wherein step (b) comprises heating to a temperature in the range from 60° C. to 75° C., preferably to a temperature in the range from 61° C. to 70° C., most preferably to a temperature in the range from 63° C. to 67° C.; and
wherein step (c) comprises heating to a temperature in the range from 82° C. to 97° C., preferably to a temperature in the range from 83° C. to 92° C., most preferably to a temperature in the range from 85° C. to 89° C.;
and comprising a subsequent step of
d) adding an ethanolic extract of hard resins from hops, in particular Xantho-Flav Pure powder and/or Xantho-Flav powder at a temperature in the range from 26° C. to 30° C.

In particular it is possible, prior to step b), to perform a step b1) comprising adding water at a temperature in the range from 40° C. to 62° C., preferably at a temperature in the range from 45° C. to 57° C., most preferably at a temperature in the range from 48° C. to 52° C.

The disclosure also relates to solubilizates which exhibit micelles in aqueous dilution loaded with curcumin alone as well as with boswellic acids alone as well as with xanthohumol alone, at least immediately after their preparation. Therefore, the disclosure also provides a method for producing a solubilizate as described above by mixing a curcumin solubilizate and a *Boswellia* solubilizate and a xanthohumol solubilizate, in particular in a quantitative ratio of 1:1:1 of the individual solubilizates.

DETAILED DESCRIPTION

The disclosure will now be explained in more detail by way of exemplary embodiments. The following components were used:

*Boswellia*

In the context of the present application, the term "*Boswellia*" in particular refers to an extract from the resin of the frankincense plant. Specifically, an extract of the species *Boswellia serrata* was used, which was an extract obtained by extraction with ethyl acetate from the resin of the plant with the botanical name *Boswellia serrata* with the product code "HC22519" manufactured by Frutarom Belgium N. V., Londerzeel, Belgium. A solubilizate containing this extract is also referred to as "boswellic acid solubilizate" because of its content of boswellic acids.

Besides extracts from the resin of the frankincense plant, it is also possible to use boswellic acids and/or derivatives of boswellic acids for the purposes of the solubilizates according to the disclosure. In particular, the following may be considered: alpha-boswellic acid (CAS number 471-66-9), beta-boswellic acid (CAS number 631-69-6) and their derivatives, 3-O-acetyl-alpha-boswellic acid (CAS number 89913-60-0), 3-O-acetyl-beta-boswellic (CAS number 5968-70-7), 11-keto-beta-boswellic acid (KBA, CAS number 17019-92-0), and 3-O-acetyl-11-keto-beta-boswellic acid (AKBA, CAS number 67416-61-9).

Curcumin

The product named "Turmeric Oleoresin Curcumin Powder 95%" with the product code EP-5001 from Green Leaf Extraction Pvt Ltd., Kerala, India, was used as the curcumin. The curcumin powder has CAS number 458-37-7. It is a natural product obtained by solvent extraction of the rhizomes of Curcuma Longa. The curcumin content of the powder is at least 95%, according to manufacturer specifications. This curcumin content is determined by ASTA method 18.0.

As an alternative to the "oleoresin turmeric 95%" curcumin powder from Green Leaf mentioned above, it is also possible for the exemplary embodiments described below to use, as the curcumin, 95% curcumin extract by Neelam Phyto-Extracts, Mumbai, India, or curcumin BCM-95-SG or curcumin BCM-95-CG from eurochem GmbH, Grobenzell, Germany, or Curcuma Oleoresin 95% from Henry Lamotte OILS GmbH, Bremen, Germany, for example.

Xanthohumol

The products "Xantho-Flav" or "Xantho-Flav Pure" of the brand "Hopsteiner" by Simon H. Steiner, Hopfen, GmbH, Mainburg, Germany were used as the xanthohumol source. Both are natural products produced from hops. The active substance is the hop polyphenol xanthohumol. This is a yellow colored powder with a xanthohumol content between 65% and 85% in "Xantho-Flav" and at least 85% in "Xantho-Flav Pure", according to manufacturer specifications. The concentrations of xanthohumol and isoxanthohumol in "Xantho-Flav Pure" are quantified by the manufacturer according to UV spectrophotometric analysis or HPLC EBC 7.8 using external calibration standard pure XN (370 nm) or IX (290 nm). "Xantho-Flav Pure" contains the prenylated flavonoid xanthohumol in a very high concentration. For the exemplary embodiments in the context of the present application, "Xantho-Flav Pure" of batch number 9432 was used.

Polysorbate 80

The source of polysorbate 80 was the material "TEGO SMO 80 V FOOD" with the specification code "K04 EU-FOOD" from Evonik Nutrition & Care GmbH, Essen, Germany. The product complies with the EU requirements for food additive E 433. As an alternative to the TEGO SMO 80 V from Evonik mentioned above, it is also possible to use TEGO SMO 80 V from InCoPA Gmbh, Illertissen, Germany, or Crillet 4/Tween 80-LQ-(SG) from CRODA GmbH, Nettetal, Germany, or Lamesorb SMO 20 and Kotilen-O/1 VL from Univar or from Kolb Distributions AG, Hedingen, Switzerland, as the polysorbate 80 in the exemplary embodiments described below.

Polysorbate 20

The source of polysorbate 20 was the material "TEGO SML 20 V FOOD" with the specification code "K09 EU-FOOD" from Evonik Nutrition & Care GmbH, Essen, Germany. The product complies with the EU requirements for food additive E 432. As an alternative to the TEGO SML 20 from Evonik mentioned above, it is also possible to use Crillet 1/Tween 20-LQ-(SG) from CRODA GmbH, Nettetal, Germany, as the polysorbate 20 within the context of the disclosure.

If water is added in the preparation of a solubilizate, distilled water is used.

Ethanol

In the context of the present application, ethanol was purchased from Berkel Pfälzische Spritfabrik GmbH & Co. KG. According to the specification for "undenatured neutral alcohol 1411U taxed", the content of ethanol of this product is about 92.6 to 95.2 wt %.

The particle size analyzes of the micelles in aqueous dilutions of solubilizates according to the disclosure were measured according to the principle of dynamic light scattering using laser light of 780 nm wavelength. The particle size measurements were performed using the ParticleMetrix NANO-flex backscatter particle analyzer. The measuring principle is based on dynamic light scattering (DLS) in a 180° heterodyne backscattering setup. With this geometry, part of the laser beam is mixed into the scattered light (heterodyne technique). Because of the short light path of 200 micrometers to 300 micrometers within the sample, backscattering is an advantage for absorbent and highly concentrated samples. The heterodyne technique has an enhancing effect on the signal-to-noise ratio and on the sensitivity of the sub-100 nm range.

The laser light is injected into the Y-fork of an optical fiber. What returns in the same fiber is the laser light partially reflected at the sapphire window of the sample chamber and the light backscattered from the sample. The detector in the second leg of the Y fork captures the interfering signals. Fast Fourier transform evaluation analyses the fluctuating stray light components to give a frequency-dependent power spectrum. Each frequency component represents a Brownian diffusion constant and can therefore be assigned to a particle size. For conversion into a particle size distribution, Stokes-Einstein relation is used:

$$D = k\frac{T}{3\pi\eta d_P}$$

This equation includes the diffusion constant D, Boltzmann's constant k, temperature T, dynamic viscosity of the medium, and the diameter $d_p$ of the particles. A temperature sensor is arranged near the sapphire window close to the sample in the measurement device.

For the experimental determination of turbidity of the solubilizates according to the disclosure, the turbidity meters are calibrated with a standard suspension. Thus, instead of measured light intensity, the concentration of the calibration suspension is indicated. So, when any arbitrary suspension is measured, the indication means that the respective liquid causes the same light scattering as the standard suspension at the indicated concentration. The internationally defined turbidity standard is formazine. The most common units include the indication FNU, i.e. Formazin Nephelometric Units. This is the unit used in water treatment, for example, for measuring at 90° in compliance with the requirements of the ISO 7072 standard.

For preparing a solubilizate according to the disclosure including the active substances curcumin and *Boswellia* it is possible to either mix individually prepared solubilizates with one another or to directly prepare a solubilizate containing curcumin and *Boswellia*. First, a preparation example using two solubilizates that were previously prepared individually will be described below.

Exemplary Embodiment 1

Solubilizate of curcumin/boswellic acid/xanthohumol

First, a 7% curcumin solubilizate is prepared. The following was used for this purpose:

| | |
|---|---|
| 925 g | polysorbate 80, |
| 75 g | 95% curcumin powder (≙71.2 g of curcumin). |

The polysorbate 80 is heated to 48 to 52° C. The curcumin powder is added to the polysorbate under stirring, while further heating to a temperature in the range from 95 to 97° C. The powder is added at an appropriate rate so as to be evenly drawn into the emulsifier during stirring. After cooling to a temperature below a maximum of 60° C., the curcumin solubilizate is bottled. This solubilizate was used for the preparation of a solubilizate comprising curcumin and *Boswellia*.

However, it should be noted that the curcumin content can be further increased without incurring adverse consequences, for example in terms of stability of the micelles. A composition consisting of 100 g of 95% curcumin powder and 900 g of polysorbate 80 results in a stable product just like a composition consisting of 120 g of 95% curcumin powder and 880 g of polysorbate 80. The preparation of these two variants corresponds to that as described above. Thus, besides a 7% solubilizate, up to 11% solubilizates can be prepared.

At a dilution ratio of 1:500 in water at pH 1.1 and a temperature of 37° C., the 7% curcumin solubilizate exhibits an averaged turbidity of 0.9 FNU.

Next, a 6% boswellic acid solubilizate was prepared. The following was used for this purpose:

| | |
|---|---|
| 76 g | 80% *Boswellia serrata* extract (≙60.8 g of boswellic acid), |
| 24 g | water, |
| 400 g | polysorbate 20. |

The water is mixed with the *Boswellia* powder while heating up to a temperature in the range from 87 to 93° C. Polysorbate 20 is incorporated while maintaining the temperature. The emulsifier is added at an appropriate rate so that the fluids are homogenized stably to form a solubilizate under stirring. Heavy foaming may occur during the preparation. This can be ignored if a clear solubilizate can be seen on the bottom of the collection vessel when bottled.

Verification of this clarity, which indicates complete micellization, is achieved by laser beam measurements. Such a laser beam measurement may be performed, for example, by illuminating the sample using a commercially available laser pointer, in particular with a wavelength in the range between 650 nm and 1700 nm (spectral color red), and subsequent visual inspection of the illuminated or irradiated solubilizate. The verification is not achieved by sampling and thus outside the reaction vessel, but in the reaction vessel. The laser beam is directed through a sight glass which is located on the front of the reaction vessel, perpendicularly to the reaction vessel. If merely a point of light appears on the rear inner surface of the reaction vessel, completely free of scattering, the resulting particle structures in the reaction vessel are smaller than the wavelength of the visible light, which is thus a visual confirmation that the process of micellization has been completed.

The product is bottled at approximately 50° C.

Finally, a 10% Xantho-Flav solubilizate (corresp. to 9.2% xanthohumol) was prepared from

| | |
|---|---|
| 100 g | Xantho-Flav Pure (≙92 g of xanthohumol), and |
| 900 g | polysorbate 80. |

For this purpose, the Xantho-Flav Pure powder is incorporated into Polysorbate 80 by stirring. The powder is added at an appropriate rate so as to be evenly drawn into the emulsifier. Homogenization is continued under heating to 83 to 87° C. Once a homogeneous solubilizate is obtained, this is followed by cooling to a temperature below 60° C. The Xantho-Flav solubilizate is then bottled and stored in the dark and cool, i.e. below 25° C.

The solubilizates of curcumin, *Boswellia*, and xanthohumol are mixed together to obtain a solubilizate that includes all three active substances.

Exemplary Embodiment 2

Instead of the xanthohumol solubilizate mentioned above, it is also possible within the scope of the disclosure to use the following solubilizate which additionally contains ethanol: 10% Xantho-Flav solubilizate (corresp. to 8% of xanthohumol) with ethanol For this variant of a xanthohumol solubilizate, the following is used:

| | |
|---|---|
| 100 g | Xantho-Flav (≙80 g of xanthohumol), |
| 150 g | ethanol (96%) neutral alcohol grade 1411U, and |
| 750 g | polysorbate 80. |

First, the Xantho-Flav powder is dissolved in ethanol while being heated to a temperature in the range between 48 and 52° C. A homogeneous solution is created. Polysorbate 80 is then added into the solution of Xantho-Flav in ethanol while heating to between 83 and 87° C. The adding is done at a rate such that the two fluids homogenize well under stirring. The resulting solubilizate is cooled to below 60° C. and is bottled and stored in the dark and cool, i.e. at temperatures below 25° C.

Exemplary Embodiment 3

Alternatively, it would also be possible to use a 7% boswellic acid solubilizate. For this purpose

| | |
|---|---|
| 82 g | 80% *Boswellia serrata* extract (≙65.6 g boswellic acid), |
| 70 g | water, |
| 350 g | polysorbate 20, |
| 441 g | polysorbate 80. | are used, which corresponds to a total amount of 943 g.

While heating to a temperature in the range from 48 to 52° C., polysorbate 20 and polysorbate 80 are homogenized with each other and thereby dissolved in each other under stirring. While maintaining the temperature, the emulsifier mixture is mixed with the water while stirring intensely enough so that the water is evenly dissolved in the emulsifier solution. At unchanged temperature, the *Boswellia serrata* extract is incorporated into the water-diluted emulsifier under stirring. The *Boswellia serrata* extract is added at a rate slow enough to be evenly drawn into the dilute emulsifier solution under stirring.

Mixing with the curcumin solubilizate described above and with one of the xanthohumol solubilizates mentioned gives a solubilizate according to the disclosure comprising curcumin, xanthohumol, and *Boswellia* as the active substances.

Exemplary Embodiment 4

For preparing a solubilizate of 2.9% curcumin/2.5% boswellic acid/3.7% xanthohumol according to exemplary example 1,

| | |
|---|---|
| 500 g | 3% curcumin solubilizate, |
| 500 g | 6% *boswellia* solubilizate, and |
| 500 g | 10% xanthohumol solubilizate | are used according to exemplary embodiment 1.

The three solubilizates are optionally heated to a temperature in the range from 50 to 60° C. to lower their viscosity, i.e. enhance flowability. The three solubilizates are homogenized by stirring to form a mixed solubilizate comprising curcumin and *Boswellia* and xanthohumol. The product is cooled to a maximum temperature of 60° C. and bottled. This product is particularly suitable for use as a capsule filling.

Exemplary Embodiment 5

Solubilizate of 3.3% Curcumin/3.6% boswellic acid with 1.8% of xanthohumol
The following is used:

| | |
|---|---|
| 45 g | 80% *Boswellia serrata* extract (36 g boswellic acid), |
| 35 g | 95% curcumin powder (33.25 g of curcumin), |
| 23 g | Xantho-Flav with at least 80% xanthohumol (18.4 g xanthohumol), |
| 60 g | water, |
| 50 g | ethanol (96%) neutral alcohol grade 1411U, |
| 350 g | polysorbate 20, |
| 437 g | polysorbate 80. |

While heating to a temperature in the range from 48 to 52° C., polysorbate 20 and polysorbate 80 are homogenized with each other while being dissolved in each other, under stirring. While maintaining the temperature, the emulsifier mixture is mixed with the water and ethanol. Stirring is performed intensely enough so that the water and the ethanol are dissolved evenly in the emulsifier solution. At unchanged temperature, the *Boswellia serrata* extract and the xanthohumol powder are incorporated into the emulsifier mixture diluted with water and ethanol, while stirring. The *Boswellia serrata* extract and the hops extract are added at a rate slow enough so as to be evenly drawn into the dilute emulsifier solution under stirring. Subsequently, the temperature is increased to a range between 63° C. and 67° C. under vigorous stirring. Then, the curcumin powder is incorporated while stirring. The temperature is further increased to a value in the range between 85° C. and 89° C. while stirring intensely enough so that the curcumin is evenly distributed in the preparation and homogenized.

This is followed by cooling to a temperature of less than or equal to 45° C.

The dark-yellow viscous preparation comprising a solubilizate of curcumin and boswellic acid and xanthohumol is then bottled and stored in the dark and cool, i.e. below 25° C.

For a particle size analysis of this solubilizate described under exemplary embodiment 5, this solubilizate was first diluted with distilled water in a ratio of 1:500 and heated to 37° C. under constant stirring using a magnetic stirrer and a hotplate. Subsequently, the pH was adjusted to 1.1 using 32% hydrochloric acid. The samples were then measured immediately. The results are summarized in the table below, for which the data of two measurements were averaged.

| | $d_{10}$ (nm) | $d_{50}$ (nm) | $d_{90}$ (nm) | $d_{99}$ (nm) |
|---|---|---|---|---|
| Intensity distribution | 10.18 | 15.70 | 533.0 | 3080 |
| Volume distribution | 7.90 | 10.96 | 15.21 | 20.37 |

After dilution in water at a ratio of 1:500 and at pH 1.1 and a temperature of 37° C., a measurement of turbidity gave a value of 1.9 FNU.

The following exemplary embodiment 6 illustrates the direct preparation of a solubilizate comprising curcumin and *Boswellia*, which contains xanthohumol in non-solubilized form, according to a further embodiment of the disclosure.

Exemplary Embodiment 6

Solubilizate of 3.3% curcumin/3.6% boswellic acid with 1.8% of xanthohumol
The following is used:

| | |
|---|---|
| 45 g | 80% *Boswellia serrata* extract (36 g boswellic acid), |
| 35 g | 95% curcumin powder (33.25 g of curcumin), |
| 23 g | Xantho-Flav with at least 80% xanthohumol (18.4 g xanthohumol), |
| 60 g | water, |
| 50 g | ethanol (96%) neutral alcohol grade 1411U, |
| 350 g | polysorbate 20, |
| 437 g | polysorbate 80. |

While heating to a temperature in the range from 48 to 52° C., polysorbate 20 and polysorbate 80 are homogenized with each other while being dissolved in each other, under stirring. While maintaining the temperature, the emulsifier mixture is mixed with the water and ethanol. Stirring is performed intensely enough so that the water and the ethanol are dissolved evenly in the emulsifier solution. At unchanged temperature, the *Boswellia serrata* extract is incorporated into the water-diluted emulsifier mixture while stirring. The *Boswellia serrata* extract is added at a rate slow enough so as to be evenly drawn into the dilute emulsifier solution, under stirring. Subsequently, the temperature is increased to a range between 63° C. and 67° C. under vigorous stirring. The curcumin powder is incorporated while stirring. The temperature is further increased to a value in the range between 85° C. and 89° C. while stirring intensely enough so that the curcumin is evenly distributed in the preparation and homogenized.

This is followed by cooling to a temperature of less than or equal to 30° C. Then, Xantho-Flav powder is incorporated while stirring. The native xanthohumol is added at a rate slow enough so as to be evenly drawn into the preparation under stirring, while the temperature is maintained in a range between 26° C. and 30° C.

Thus, in this exemplary embodiment, in contrast to curcumin and boswellic acid, xanthohumol is contained in non-micellated form, but rather exclusively in its native form, because at low temperatures micelles cannot form from powdery raw materials. This has been found and verified by respective particle measurements (two clearly different fractions).

The dark-yellow viscous preparation comprising a solubilizate of curcumin and boswellic acid with native xanthohumol is then bottled and stored in the dark and cool, i.e. below 25° C.

The following solubilizate of curcumin and boswellic acid may likewise be used as a basis for adding xanthohumol in native form, in the same way as in exemplary embodiment 6.

The weight percentages of curcumin and boswellic acids and of xanthohumol in the final product are then obtained by adjusting the amount of xanthohumol added.

Exemplary Embodiment 7

Solubilizate of 5.4 curcumin/6.6% boswellic acid as a basis for a product including native xanthohumol This further embodiment of the solubilizate according to the disclosure with native xanthohumol was also prepared directly. As with the curcumin-boswellic acid solubilizate described above, the active substances were co-micellated here as well. The following was used for this purpose:

| | |
|---|---|
| 82 g | 80% *boswellia serrata* extract (=65.6 g boswellic acid), |
| 57 g | 95% curcumin powder (=54.1 g of curcumin), |
| 70 g | water, |
| 350 g | polysorbate 20, |
| 441 g | polysorbate 80. |

The solubilizate of 5.4 curcumin/6.6% boswellic acid was prepared in the same way as the preparation of the curcumin-boswellic acid solubilizate in exemplary embodiment 6 described above.

After cooling to a temperature of less than or equal to 30° C., Xantho-Flav powder is incorporated in the desired amount while stirring. The native xanthohumol is added at a rate slow enough so as to be evenly drawn into the preparation under stirring, while the temperature is maintained in a range between 26° C. and 30° C.

At low temperatures, no product micelle can form. Xanthohumol is therefore only present in native and not in micellated form in this exemplary embodiment. This is found and verified in a respective particle measurement showing two clearly different fractions.

The dark-yellow viscous preparation comprising a solubilizate of curcumin and boswellic acid with native xanthohumol is then bottled and stored in the dark and cool, i.e. below 25° C.

Depending on the application case, it is also possible within the scope of the disclosure for the contents of curcumin and *Boswellia* extract and xanthohumol in the particular solubilizates to be adjusted so as to be significantly higher than in the discussed example.

If higher loads in active substances are adjusted in the solubilizate prior to or without the addition of native xanthohumol, this is limited by the fact that an emulsion will be produced instead of a solubilizate when a content of active substances specific for the respective composition is exceeded. When the content of active substances is increased, the respective contents of the other components (in wt %) are necessarily reduced.

Above a specific limit, a disperse system is obtained which, however, is not irreversibly soluble in water like the solubilizates according to the disclosure, and which does not exhibit the very low turbidity measured for these solubilizates under physiological conditions of the gastric passage, i.e. under physiological conditions (pH 1.1 and 37° C.). This is the case for the xanthohumol within the scope of the inventive variant of adding native xanthohumol without solubilizing it. However, curcumin and *Boswellia* are again solubilized in the form of micelles in this variant.

If the content in curcumin or *Boswellia* and/or optionally xanthohumol is chosen too high, dispersions will be formed. These might be (nano)emulsions, however, in terms of the respective one or more active substance(s) these are not solubilizates in which the active substance(s) are contained in the very small micelles. However, according to the inventor's experience, only the solubilizates provide for the significantly increased bioavailability of the one or more active substance(s) according to the disclosure, even if an emulsion allowed for a higher load in active substances. Surprisingly, though, it has also proven to be advantageous to administer non-solubilized xanthohumol together with curcumin and boswellic acid in a solubilizate.

The transparent and completely stably water-soluble formulation according to the disclosure exhibits steady transparency, in gelatin-free capsules (hard and/or soft) and in water-based liquid end products, regardless of pH, without additives as in soft and hard gelatin capsules. Products exhibiting such transparency and water solubility are urgently sought by the relevant industry for innovative products as a capsule filling. To the best of the inventor's knowledge, there has not yet been a formulation of curcumin with *Boswellia*, i.e. with at least one boswellic acid and/or at least one boswellic acid derivative, and with xanthohumol, which meets these requirements.

As a result of the formulation according to the disclosure in a solubilizate with very small, stable and gastric acid-resistant micelles, the disclosure provides a solubilizate of curcumin with *Boswellia* and xanthohumol for use as a dietary supplement and/or as a pharmaceutical drug, in particular for use as a dietary supplement and/or as a pharmaceutical drug with an anti-inflammatory effect.

It will be apparent to a person skilled in the art that the disclosure is not limited to the examples described above, but rather can be varied in multiple ways. It is in particular possible for the features of the individually illustrated examples to be combined or swapped.

The invention claimed is:

1. A solubilizate, comprising:
   3 wt % to 10 wt % curcumin;
   3 wt % to 10 wt % of one or more boswellic acids and/or one or more boswellic acid derivatives;
   1 wt % to 10 wt % xanthohumol; and
   at least one emulsifier, namely polysorbate 80 or polysorbate 20 or a mixture of polysorbate 20 and polysorbate 80,
   wherein the emulsifier content is at least 70 wt %.

2. The solubilizate according to claim 1, comprising 3 wt % to 8 wt % curcumin.

3. The solubilizate according to claim 1, comprising 3 wt % to 7 wt % curcumin.

4. The solubilizate according to claim 1, wherein the one or more boswellic acids and/or one or more boswellic acid derivatives comprise one or more of 11 keto-β-boswellic acid, KBA, (CAS 17019-92-0), 3-O-acetyl-11-keto-β-boswellic acid, AKBA, (CAS 67416-16-9), 3-O-acetyl-α-boswellic acid, AαBA, and 3-O-acetyl-β-boswellic acid, AβBA.

5. The solubilizate according to claim 1, comprising 3 wt % to 8 wt % of the one or more boswellic acids and/or one or more boswellic acid derivatives.

6. The solubilizate according to claim 1, comprising 3 wt % to 6.6 wt % of the one or more boswellic acids and/or one or more boswellic acid derivatives.

7. The solubilizate according to claim 1, comprising 1 wt % to 5 wt % xanthohumol.

8. The solubilizate according to claim 1, comprising 1 wt % to 3 wt % xanthohumol.

9. The solubilizate according to claim 1, wherein the emulsifier content is in a range between 75 wt % and 95 wt %.

10. The solubilizate according to claim 1, wherein the emulsifier content is in a range between 79 wt % and 88 wt %.

11. The solubilizate according to claim 1, wherein
the solubilizate contains an extract from a resin of a *Boswellia serrata* plant obtained by extraction with ethyl acetate, as a source for the one or more boswellic acids and/or one or more boswellic acid derivatives, wherein this extract contains boswellic acids in a concentration of at least 85 wt %.

12. The solubilizate according to claim 1, wherein
a ratio of emulsifier to boswellic acids and/or to boswellic acids and at least one of their derivatives is in a range between 20:1 and 3:1.

13. The solubilizate according to claim 1, wherein
a ratio of emulsifier to curcumin is in a range between 30:1 and 3:1.

14. The solubilizate according to claim 1, wherein
a ratio of emulsifier to xanthohumol is in a range between 30:1 and 3:1.

15. The solubilizate according to claim 1, wherein
the solubilizate contains up to 20 wt % of ethanol.

16. The solubilizate according to claim 1, wherein
a diameter distribution of micelles in a dilution of the solubilizate with distilled water in a ratio of 1:500 at pH 1.1 and 37° C. is in a range from $d_{10}=6$ nm to $d_{90}=16$ nm.

17. The solubilizate according to claim 1, wherein
the solubilizate exhibits a turbidity of less than 25 FNU, measured by scattered light measurement using infrared light according to the specifications of the ISO 7027 standard at a dilution of the solubilizate in a ratio of 1:50 in water under physiological conditions (pH 1.1 and 37° C.).

18. The solubilizate according to claim 1, wherein
the solubilizate contains the xanthohumol in non-solubilized form.

19. A capsule filled with the solubilizate according to claim 1.

20. A fluid, containing the solubilizate according to claim 1,
wherein
the fluid is selected from the group consisting of foods, dietary supplements, beverages, cosmetics, and pharmaceutical products.

21. The fluid of claim 20, wherein
the fluid comprises an aqueous dilution of the solubilizate.

* * * * *